United States Patent [19]

Self

[11] Patent Number: 4,840,895
[45] Date of Patent: * Jun. 20, 1989

[54] MONOCLONAL ANTIBODIES REACTIVE WITH IMMUNE COMPLEXES

[75] Inventor: Colin H. Self, London, England

[73] Assignee: Cambridge Patent Development Limited, United Kingdom

[*] Notice: The portion of the term of this patent subsequent to May 9, 2006 has been disclaimed.

[21] Appl. No.: 803,137

[22] PCT Filed: Mar. 29, 1985

[86] PCT No.: PCT/GB85/00120
§ 371 Date: Nov. 18, 1985
§ 102(e) Date: Nov. 18, 1985

[87] PCT Pub. No.: WO85/04422
PCT Pub. Date: Oct. 10, 1985

[30] Foreign Application Priority Data

Mar. 30, 1984 [GB] United Kingdom ............... 8408193

[51] Int. Cl.⁴ .............................. G01N 33/53
[52] U.S. Cl. .......................................... 435/7; 435/18; 435/21; 435/26; 435/28; 436/500; 436/507; 436/512; 436/518; 436/536; 436/548; 436/800; 436/804; 436/805; 436/808; 935/110; 530/387; 530/388; 530/808
[58] Field of Search ................. 435/7, 21, 26, 28, 18; 436/548, 500, 518, 507, 512, 536, 800, 804, 805, 808; 530/387, 388, 808; 424/85, 88; 935/110

[56] References Cited

U.S. PATENT DOCUMENTS 4,510,239  4/1985  Miller et al. ............... 436/548
4,544,640 10/1985  Soma et al. ................ 436/506
4,606,855  8/1986  Deutsch et al. ........... 436/548
4,670,383  6/1987  Baier et al. .................. 435/7

OTHER PUBLICATIONS

D. A. Nemazee et al., Proc. Natl. Acad. Sci. USA, 79, pp. 3828-3832, Jun., 1982.
Science, vol. 218, Oct. 29, 1982, p. 474.

Primary Examiner—Robert J. Warden
Assistant Examiner—Robert Benson
Attorney, Agent, or Firm—Jacobs & Jacobs

[57] ABSTRACT

A secondary monoclonal antibody against a complex of a molecule of molecular weight less than 5000 and a binding protein against said molecule which secondary monoclonal antibody is not an antibody against molecule or against its binding protein.

78 Claims, No Drawings

MONOCLONAL ANTIBODIES REACTIVE WITH IMMUNE COMPLEXES

The present invention relates to a class of monoclonal antibodies, which may be free or present in a complex, to the manufacture of such antibodies and to their use in reactions which employ an antigen-antibody reaction.

Reactions between an antigen and its antibody have found many applications in biotechnology and especially in diagnostic tests, for example medical diagnostic tests, gene probes and the like. Monoclonal antibodies (see for example G. Galfre and C. Milstein, Methods in Enzymology, 73, 3–57, 1981) have been found to be of particular use in biotechnology and especially in diagnostic tests.

A monoclonal antibody was described by D. A. Nemazee and V. J. Sato (see Proc. Natl. Acad. Sci. USA, V2, 79, pp 3828–3832, 1982) which was an antibody against a complex of two other antibodies as a result of exposing a new epitope in the Fc region of one of the original antibodies. Since the original antibodies were both macromolecules conformational changes in the Fc region was not unexpected. Similar changes would not be expected to occur if a small molecule had been employed. Similarly since small molecules cannot have simultaneous multiple epitopes and cannot thus themselves bind more than one antibody, (for example see R. J. Thompson and A. P. Jackson, TIBS, 9, pp1–3, 1984) the effect described by Nemazee and Sato would not be expected if a complex employing a small molecule was used. Contrary to this expectation, it has now been found that, possibly because of a different mechanism, a new class of monoclonal antibody can be made which are surprisingly useful in biotechnology, for example in diagnostic tests.

Accordingly the present invention provided a monoclonal antibody characterised in that said monoclonal antibody is a secondary monoclonal antibody against a complex of a small molecule and a binding protein against said small molecule which secondary antibody is not an antibody against the small molecule or against its binding protein.

When used herein the term "small molecule" means a molecule of molecular weight less than 5000. Such small molecules most aptly have a molecular weight of less than 2000 and preferably have a molecular weight of less than 1200.

Proteins used in this invention may be antibodies or other proteinaceous materials such as enzymes, binding proteins such as steroid binding proteins or vitamin binding proteins. Preferably the protein used in this invention is a monoclonal antibody in which case the small molecule may be termed herein a small antigen.

The skilled art worker will appreciate that low molecular weight materials such as the small molecules used in this invention are normally non-immunogenic but that antibodies thereto can be obtained by immunising an animal with a conjugate of the non-immunogenic molecule (or a very close analogue) and an immunogenic material such as bovine serum albumin or an equivalent agent. The desired antibody may then be obtained by methods known per se.

Accordingly, in a preferred form, the present invention provides a monoclonal antibody characterised in that said monoclonal antibody is a secondary monoclonal antibody against a complex of a small antigen and a monoclonal antibody against the small antigen which secondary monoclonal antibody is not an antibody against the small antigen or against its monoclonal antibody.

When used hereinafter the term "secondary monoclonal antibody" will mean an antibody provided by this invention as defined above. When used hereinafter the term "primary monoclonal antibody" will mean the monoclonal antibody against the antigen (that is a conventional monoclonal antibody).

The monoclonal antibody may be the complete immunoglobulin or fragment thereof having the described binding activity. As will become apparent hereinafter, certain embodiments of this invention will benefit more from the use of the complete immunoglobulin than from a fragment thereof whereas other embodiments will benefit more from the use of fragments of the complete immunoglobulin such as the Fab and $F(ab')_2$ fragments. This reflects the view that the binding between the secondary antibody and the complex takes place at or about the site of binding of the small molecule.

When it is stated the secondary monoclonal antibody is not an antibody against the small antigen or its binding protein antibody (the primary monoclonal antibody) then generally the secondary monoclonal antibody and small antigen or binding protein have an equilibrium constant of less than $10^3$ liters per mole, more favourably less than $10^{2.5}$ liters per mole and preferably less than $10^2$ liters per mole. Normally the secondary monoclonal antibody will not bind the small antigen or primary monoclonal antibody to a greater extent that it will bind unrelated small molecules or proteins. The secondary monoclonal antibody and the complex of small antigen and primary monoclonal antibody will suitably have an equilibrium constant of at least $10^4$ liters per mole, favourably at least $10^5$ liters per mole, more favourably at least $10^6$ liters per mole and preferably at least $10^7$ liters per mole.

The preceeding statements are also believed to apply to in an analogous manner to other small molecules binding to binding proteins.

It is now believed that the ratio of equilibrium constants between (a) the secondary monoclonal antibody and the complex and (b) the secondary monoclonal antibody and either component of the complex should be greater than 100:1, more suitably greater than 1,000:1 and preferably greater than 10,000:1.

A suitable method of selection of a secondary monoclonal antibody (that is one which is not an antibody against a small antigen or a primary monoclonal antibody against said small antigen but is a monoclonal antibody against a complex of the antigen with the primary monoclonal antibody) is as follows:

1a. The possible secondary monoclonal antibody is bound to a solid surface such as the inside of polystyrene test tubes.

1b. Each member of the tubes is given the same amount of labelled primary monoclonal antibody (for example radio-labelled).

1c. A range of concentrations of antigen is made and a different concentration added to each of the tubes, one tube receiving none.

1d. The tubes are incubated.

1e. Unbound material is washed from the tubes.

1f. The retained label is measured.

Where the amount of retained label in the tube which received no antigen is less than a small fraction (such as less than 1%, more suitably less than 0.1% and preferably less than 0.01%) of the greatest amount of label retained in any of the tubes, it is considered that the secondary monoclonal antibody is not an antibody against the small antigen or the primary monoclonal antibody but is a monoclonal antibody against the primary monoclonal-antigen complex.

As will be understood by the skilled worker small molecules are not normally antigenic but as confirmation that the secondary monoclonal antibody will not bind the small molecule the following confirmatory test may be employed.

2a. The possible secondary monoclonal antibody is bound to a solid surface such as the inside of polystryene test tubes.

2b. Each member of a group of the tubes is given the same labelled antigen (for example radio-labelled).

2c. A range of concentrations of primary monoclonal antibody against the small antigen is made and a different concentration added to each of the tubes, one tube receiving none.

2d. The tubes are incubated.

2e. unbound material is washed from the tubes.

2f. The retained label is measured.

Where the amount of retained label in the tube which received no primary monoclonal antibody is less than a small fraction (such as less than 1%, more suitably less than 0.1% and preferably less than 0.01%) of the greatest amount of label retained in any of the tubes, then the possible secondary monoclonal antibody is considered not to be an antibody to the small antigen.

Analagous procedures may be employed for small molecules and binding proteins other than small antigens and primary monoclonal antibodies.

A favoured use of the secondary antibodies of this invention is in diagnostic tests. Reduction in reversibility in reactions can lead to higher apparent affinity between ligand and antiligand which can lead to improved stability to washing, faster reaction times and the like. Also use of a secondary monoclonal antibody of this invention can allow small molecules to be determined by non-competitive methods such as Sandwich methods which can operate over a wider range of concentrations and can be less sensitive to the nature and mode of use of the reagents. This will be apparent hereinafter.

One class of small antigens which are useful diagnostically include hormones. Particularly relevent hormones include thyroid hormones and steroidal hormones such as progesterone and estrogen. Other favoured steroids include hydrocortisone, testosterone, oestradiol, oestratriol and androstanediol.

Thus in a particularly apt aspect this invention provides a monoclonal antibody against a complex of a hormone and a monoclonal antibody to said hormone which monoclonal antibody is not an antibody against the hormone or against the said antibody to said hormone.

Yet other antigens of particular interest which form complexes with antibodies are medicaments. Such medicaments include antibiotics such as the aminoglycosides such as gentamicin, cardioactives such as digoxin and the like. Drugs of abase may similarly be determined.

Thus in a particularly apt aspect this invention provides a monoclonal antibody against a complex of a medicament and a monoclonal antibody to said medicament which monoclonal antibody is not an antibody against the medicament or against said antibody to said medicament.

Since a highly preferred use of the secondary monoclonal antibody is in diagnostic tests, it is preferable that the monoclonal antibody of this invention or the antigen-antibody complex comprise a signal generating means. The signal generating means may be any which allows the presence of a complex between the secondary monoclonal antibody and the small antigen-antibody complex to be determined. The signal generating means may be one which is directly determinable (for example a radio-active label) or one which is indirectly determinable (for example an enzyme label the presence of which gives rise to an event which is itself determinable). If the signal generating means is present in the small antigen-antibody complex it is most suitably present as a label on the antibody. However, more favourably the signal generating means is present in the secondary monoclonal antibody of this invention.

From the foregoing it will be understood that in a particular desirable aspect this invention provides a monoclonal antibody labelled with a signal generating means characterised in that said monoclonal antibody is one against a small antigen monoclonal antibody complex which monoclonal antibody is not an antibody against said small antigen or against its monoclonal antibody.

Similarly it will be understood that in a desirable aspect this invention provides a monoclonal antibody characterised in that said monoclonal antibody is one against a small antigen monoclonal antibody complex which monoclonal antibody is not an antibody against said small antigen or against its monoclonal antibody and said complex is labelled with a signal generating means.

Suitable methods of labelling include those set forth by P. R. Raggatt and C. N. Hales in "Immunoassays using labelled antigens or antibodies" in Clinical Aspects of Immunology, Ed. Peters and Lachman, Blackwell Scientific Publications, Oxford, 1983.

If a radiolabel is employed as signal generating means the label may be induced into material by employing conventional techniques such as producing an antibody by in-vitro biosynthesis employing radiolabelled precursors or by labelling of an already formed antibody, for example by iodination with radioactive iodine for example by use of lactoperoxidase iodination.

An alternative directly determinable signal generating means is a flourescent label, for example flourescein with which the antigen or antibody may be labelled by reaction with flourescein isothiocyanate or the like.

A preferred method of labelling an antigen or antibody with a signal generating means is to label it with an enzyme which can give rise to a determinable event such as a colour change or change in spectral properties (for example in the u.v. region). The enzyme label may be introduced in any convenient manner such as coupling to the antibody or antigen by using a bifunctional reagent such as glutaraldehyde.

Favoured enzyme labels include phosphatase, peroxidase $\beta$-galactosidase, lysozyme and dehydrogenases such as malate and glucose-6-phosphate. Phosphatases may be observed by their ability to dephosphorylate compounds to yield materials which are detected. Peroxidase may be observed by their ability to give rise to hydrogen peroxide which may be detected. $\beta$-galactosidase may be observed by their ability to hydrolyse $\beta$-galactosides to give rise to detectable procucts. Lysozyme may be observed by its ability to rupture bacterial cells which can give rise to turbidity changes. Dehydrogenases may be observed by its ability to give rise to the change in the oxidative state of NAD and NADH.

Favoured enzyme labels include acid and alkaline phosphatases. A preferred enzyme label is alkaline phosphatase.

Such conjugated phosphatase may be employed to dephosphorylate materials such as dinitrophenol to produce a readily detectable change. It is also known that such conjugated phosphatases may be employed to convert NADP to NAD which them starts a cyclic chemical reation which leads to a readily determinable change.

A favoured enzyme label is acid phosphatase. A preferred enzyme label is alkaline phosphatase.

Another apt method of labelling an antigen or antibody with a signal generating means is to label it with a material capable of giving rise the chemiluminescence, for example by any convenient art method.

Hereinafter unless otherwise indicated the term "antigen" refers to "small antigen".

As previously indicated this invention is most aptly adapted to methods of diagnosing materials. Thus the present invention provides a method of determining a member of a small molecule binding protein pair which method comprises contacting a suspected source of a member of the pair and with a secondary monoclonal antibody to the complex of the pair and mesuring the association between the member of the pair to to be determined and the other member of the pair or the secondary monoclonal antibody.

Since in a favoured form the small molecule is a small antigen and the binding protein is a monoclonal antibody, in a further favoured aspect the present invention provides a method of determining a member of antigen primary monoclonal antibody pair which method comprises contacting a suspected source of the member pair with the other member of the pair and with a secondary monoclonal antibody to the complex of the pair and measuring the asssociation between the member of the pair to be determined and the other member of the pair or the secondary monoclonal antibody.

The measurement of the association between the member of the pair to be determined and the other member of the pair or the secondary monoclonal antibody may be qualitative or quantitative but is most beneficially quatitative. Any suitable method may be employed which will measure the binding of an antibody to its antigen, for example by immobilising one component on a solid substrate and measuring the amount of the other component which becomes bound to the solid substrate; or by binding one component to an enzyme which enzyme's activity is altered when another component binds to the first component; or agglutination; or by precipitation.

As previously indicated the member of the pair added to the reaction or the secondary monoclonal antibody may be labelled with a signal generating means. This signal generating means can be employed to measure the association of the materials.

Since it preferred to employ a secondary monoclonal antibody which is labelled with signal generating means in a favoured aspect a method of determining a member of an antigen primary monoclonal antibody pair which method comprises contacting a suspected source of the member of the pair with the other member of the pair and with a secondary monoclonal antibody to the complex of the pair which secondary monoclonal antibody is labelled with signal generating means and measuring the association between the member of the pair to be determined and the secondary monoclonal antibody which measurement employs the signal generating means.

The determination method of this invention may be adapted to the determination of the small antigen or its primary monoclonal antibody. However, the method of this invention is most favourably adapted to the determination of an antigen. Thus in a favoured aspect the present invention provides a method of determining an antigen which method comprises contacting a suspected source of the antigen with a primary monoclonal antibody to said antigen and with a secondary monoclonal antibody to the complex of said antigen and primary monoclonal antibody and measuring the association between the antigen and the primary or secondary monoclonal antibody.

The measurement of the association is most aptly carried out employing a signal generation means with which either the primary or secondary monoclonal antibody is labelled. However, as previously indicated it is preferred to employ a secondary monoclonal antibody which is labelled with a signal generation means.

Thus in a preferred aspect, the present invention provides a method of determining an antigen which method comprises contacting a suspected source of said antigen with a primary monoclonal antibody to said antigen and with a secondary monoclonal antibody to the complex of the antigen and its primary monoclonal antibody which secondary monoclonal antibody is labelled with signal generating means and measuring the association between the antigen and the secondary monoclonal antibody which measurement employs the signal generating means.

The source of the material to be determined is normally a biologically derived fluid such as blood, serum, plasma, urine, milk, saliva or tissue extracts or fluid materials derived from the food industry. Thus for example diagnostic tests may be carried out for the materials hereinbefore described using the appropriate secondary antibody.

In one particularly apt form of this invention a member of the antigen primary antibody pair is bound to a surface, a suspected source of the other member of the pair is brought into contact with the surface and the secondary monoclonal antibody labelled with signal generating means is also brought into contact with the surface, the system is incubated until the other member of the pair and the secondary monoclonal antibody become bound to the first member of the pair and hence to the surface, the liquid is separated from the surface and the signal generating means is employed to measure the secondary monoclonal antibody thereby determining the amount bound and hence the amount of the member of the pair to be determined.

Normally and preferably the secondary monoclonal antibody which is measured is that fraction which becomes bound to the surface (as opposed to measuring the amount remaining in solution which is a less suitable method.)

Most suitably this aspect of the invention is adapted to determine an antigen so that the member of the pair to be bound to the surface is the primary monoclonal antibody.

Thus in a highly favoured form, this invention provides a method of determining an antigen in a source suspected of containing it which comprises binding a primary monoclonal antibody to said antigen to a surface, contacting the thus bound primary monoclonal antibody with the suspected source of antigen and with a secondary monoclonal antibody labelled with signal generating means, incubating the system until antigen and secondary monoclonal antibody become bound to the primary antibody and hence to the surface, separating the liquid from the surface and determining the secondary monoclonal antibody on the surface by employing the signal generating means.

In an alternative apt form of this invention a secondary monoclonal antibody to a complex of a antigen and a primary monoclonal antibody one of which is labelled with a signal generating means is bound to the surface, a suspected source of one member of the complex is brought into contact with the surface and the other member of the complex is brought into contact with the surface, the system is incubated until complex is formed and becomes bound to the secondary monoclonal antibody and hence to the surface, the liquid is separated from the surface and the signal generating means is employed to measure the complex bound and hence the amount of the member of the complex to be determined.

Normally and preferably that fraction of the complex which is measured is that fraction which becomes bound to the surface (as opposed to measuring the amount remaining in solution which is a less suitable method).

Preferably the preceding method is adapted to the determination of an antigen so that the primary monoclonal antibody is labelled with the signal generating means.

Thus in a favoured form, this invention provides a method of determining an antigen in a source suspected of containing it which comprises binding a secondary monoclonal antibody to a surface which secondary monoclonal antibody is one against a complex of the antigen and a primary monoclonal antibody labelled with signal generating means, contacting the thus bound secondary monoclonal antibody with the suspected source of antigen and with labelled primary monoclonal antibody, incubating the system until antigen and labelled primary monoclonal antibody become bound to the secondary monoclonal antibody, separating the liquid from the surface and determining the primary monoclonal antibody on the surface by employing the signal generating means and hence determining the antigen.

Although these methods of the invention employing surfaces offer advantages for molecules in the 1200-5000 molecular weight range the advantages are particularly marked when employed in the determination of small antigens below 1200 (since small antigens could not hitherto be readily determined by ELISA or analogous assays.)

In yet another aspect, this invention provides a method of determining an antigen monoclonal antibody pair which method comprises binding one of the pair to a surface and contacting that surface with a suspected source of the other member of the pair, a secondary monoclonal antibody to the complex of the pair and the other member of the pair labelled with signal generating means, incubating the system, separate the liquid from the surface and measuring the association between the labelled component and the surface and thereby determining the amount of substance to be determined present in the source suspected of containing it. Normally this involves comparing the amount of labelled component which becomes bound to the amount which becomes bound in the presence of known amounts of the unlabelled material to be determined.

Normally it is preferred to adapt this method to the detection of antigen in which case the primary antibody is bound to the surface. Preferably the retained label bound to the surface is determined (as opposed to the fraction remaining in solution).

The secondary monoclonal antibodies of this invention may also be employed in diagnostic tests employing agglutination.

In one suitable aspect the present invention provides a method of determining an antigen which method comprises binding the antigen to solid particles, contacting said antigen bound particles with a suspected source of antigen and with a secondary monoclonal antibody to a complex of antigen and a primary monoclonal antibody thereto and measuring the resulting agglutination. If antigen is present in the source a reduction in the amount of agglutination occurs which may be used to indicate the amount of antigen in the source.

In a less favoured agglutination test, a primary monoclonal antibody is bound to particles and contacted with the secondary monoclonal antibody and a suspected source of antigen. In such a test the amount of agglutination is indicative of the amount of antigen in the test sample.

The determinations of this invention will normally be performed under conventional conditions for such determinations, for example at a temperature of 4°–45° C., more usually 15°–38° C. and preferably at 18°–25° C.; in aqueous solutions which are generally substantially isotonic; and at a pH of 2–10, more usually 5–9, preferably 6–8 and most preferably at about 7.

The secondary monoclonal antibodies of this invention may be made by forming a complex between an antigen (or other small molecule) and its monoclonal antibody, (or other binding protein) the complex is then used as an immunogen to raise monoclonal antibodies by methods known per se.

Syngeneic animals may advantageously be employed to provide the secondary monoclonal antibody (i.e. syngeneic with respect to the animals employed to raise the primary antibody).

The selection of cell lines producing the secondary monoclonal antibody may be as hereinbefore described and essentially involves selecting cell lines which do not produce antibody against the antigen or its primary monoclonal antibody but which do produce antibody against the complex.

This invention with respect to diagnostic methods also extends to determinations of small molecules which form complexes with binding proteins in analogous manner to the hereinbefore described methods employing small antigens and their antibodies.

Most aptly the small antigens and other small molecules employed in or determined by a method of this invention are those which are soluble in water since this eases complex formation. Such molecules generally have hydroxyl, amino or carboxyl groups. Complexes (for immunisation) may be prepared by dissolving or intimitely dispersing the small molecule and binding protein together in aqueous media. Generally a large excess of the small molecule is employed. The complexes may be injected in solution optionally together with an adjuvent such as complete or incomplete freunds adjuvent. The complexes may also be employed in precipated form.

The present invention also extends to diagnostic kits which incorporate a secondary monoclonal antibody of this invention. Preferred kits will comprise a labelled secondary monoclonal antibody of this invention. Most aptly the kits of this invention will comprise an antibody of this invention in the form of a solid (eg in a bottle) or absorbed into or onto a solid surface (eg a well on a plate).

In one method of this invention primary antibody may be on the surface of a well or other isolating surface, the solution to be determined is contacted with that surface for sufficient time for small antigen to become bound to the surface, optionally the solution is removed from the surface, labelled secondary antibody is introduced and the solution incubated. The solution is seperated from the solid surface which is then washed and the bound label determined. In an alternative method the solution to be determined and the secondary antibody are added at essentially the same time. In yet another method the labelled secondary antibody is present before the introduction of the solution to be determined.

In analogous manner labelled primary antibody may be employed.

Complexes of a small antigen and a primary monoclonal antibody may be rendered more immunogenic if the primary monoclonal antibody is first conjugated with an antigenic material such as alkaline phosphatase. Thus in a preferred form the complex used to raise the secondary monoclonal antibody is a complex including a primary monoclonal antibody conjugated with an antigenic material such as alkaline phosphatase.

The following examples illustrate the invention.

EXAMPLES

In the following examples monoclonal antibodies against the different materials described are made and their affinities determined by means of standard techniques, as described in Soos, M. & K. Siddle, The Journal of Immunological Methods, 1982, 51, 57–68. The Conjugation to alkaline phosphatase is performed according to E. Engvall & P. Perlmann, 1971, Immunochemistry, 8, 871.

EXAMPLE 1

Preparation of a secondary monoclonal antibody against a complex of progesterone and a labelled primary monoclonal antibody against progesterone, said secondary monoclonal antibody not being an antibody against progesterone or the primary monoclonal antibody against progesterone.

Monoclonal antibody against progesterone (MabProg) is made using as immunogen progesterone-HS-Bovine serum albumin. MabProg is conjugated to purified calf intestinal alkaline phosphatase.

A 1 ml solution of 150 ug of this MabProg-alkaline phosphatase conjugate (MabProg-AP) in phosphate buffered saline at pH 7.4 is then slowly mixed with constant gentle stirring with a 0.1 ml solution of 100 ug progesterone (prog). The mixture is left gently stirred at room temperature (23° C.) for 1 hour and then left at 4° C. for twelve hours, or as long as required, yielding the MabProg-AP-prog complex. It is then used as immunogen in inbred mice syngeneic to that from which the original mocolonal antibody was derived. The same hybridoma techniques as above are employed to give rise to cell lines producing monoclonal antibodies to the antibody-antigen complex (secondary monoclonal antibody—MabSEC). Culture fluids of these cell lines are then screened for their reactivity to progesterone alone in terms of their equilibrium constants. Those cell lines producing antibody reactive with progesterone with an equilibrium constant of greater than $10^3$ liters/mole are discarded. Those remaining are tested for their utility in determination of progesterone as in the following example.

EXAMPLE 2

Determination of progesterone using a secondary monoclonal antibody.

The wells of polystyrene microtitre plates are coated with a primary monoclonal antibody against progesterone by conventional technique. Standard progesterone solutions covering the range 0 to 100 ng/ml progesterone are made for example in progesterone-free human serum. One hundred ul of each solution is added to separate wells. One hundred ul of each sample upon which a progesterone determination is to be made is added to separate wells. One hundred ul of a solution of 50 ng/ml purified secondary monoclonal antibody against a complex of progesterone (as described before) and the primary monoclonal against progesterone and which has been conjugated to alkaline phosphatase by glutaraldehyde using are methods (as described herein) is added to each well, mixed and the microtitre plates incubated for one hour at 37° C. Unbound material is shaken free and the wells washed four times with Tris-buffered normal saline at pH 7.4 containing 0.05% Tween 20. To each well is then added 200 ul of 5 mM para-nitrophenol phosphate in 0.15M carbonate buffer at pH 10.3 containing 3.3 mM magnesium chloride. The plates are incubated at room temperature and the formation of para-nitrophenol followed by the absorbance increase of the solutions at 405 nM. The incubation is continued until the greatest absorbance change is 1.5 optical density units whereupon all of the wells are read at this time and a standard curve of progesterone concentration against absorbance change is drawn from the results of the wells receiving the standard solutions. From this the absorbance changes of the wells receiving the samples to be determined are converted into progesterone concentrations.

EXAMPLE 3

In an alternative to example 1 the complex of progesterone and the labelled monoclonal antibody against it may be formed by dialysing the 1 ml solution of 150 ug of the MabProg-AP in phosphatase buffered saline for seven days at 4° C. against 5 liters of the same buffer in which 10 mg of progesterone is constantly mixed.

EXAMPLE 4

Preparation and selection of a secondary monoclonal antibody of use in the assay of propranolol.

Primary monoclonal antibody against propranolol (MabProp) is obtained using an immunogen consisting of a propranolol-bovine serum albumin conjugate made with N-(4-bromobutyl)phthalimate (Sigma Chemical Co. London catalogue number B 3502) by conventional means. The antibody is conjugated to purified calf intestinal alkaline phosphatase. A 1 ml solution of 150 ug of this MabProp-alkaline phosphatase conjugate (MabProp-AP) in phosphate buffered saline at pH 7.4 is then slowly mixed with constant gentle stirring with a 0.1 ml solution of 100 ug propranolol (prop). The mixture is left gently stirred at room temperature (23° C.) for 1 hour and then left at 4° C. for twelve hours, yielding the MabProp-AP-prop complex. This is then used as immunogen in inbred mice syngeneic to that from which the original monoclonal antibody was derived. The same hybridoma techniques as above are employed to give rise to cell lines producing monoclonal antibodies to the antibody-antigen complex (MabSEC). Culture fluids of these cell lines are then screened for their utility in the assay of propranolol as follows:

Wells of a micro-ELISA plate are coated with MabSEC by incubating 200 ul of a solution consisting of 100 ng/ml the antibody in 50 mM bicarbonate buffer pH 9.6 in each well for four hours at temperature (23° C.). The solution is then tapped out and replaced with 200 ul of 2% lactalbumin in the same buffer, the plate left for a further four hours at room temperature and then the wells washed four times with 50 mM Tris pH 7.4 containing N saline and 0.02% Tween 20. Solutions of propranolol in 50 mM Tris-bufferd saline at pH 7.4 are made containing 0.1 ng/ml, 1 ng/ml, 10 ng/ml, 100 ng/ml and 0 propranolol. 0.3 ml of each individual solution is mixed with an equal volume of a 50 ng/ml solution of the MabProp-AP conjugate in 50 mM Tris-saline buffer at pH 7.4 and incubated for one hour at room temperature. 200 ul of each of these mixtures is put into duplicate wells in the coated microtitre plate and then incubated at room temperature for a further hour. The solutions are then shaken out of the wells and the wells washed four times with Tris-buffered saline containing 0.05% Tween 20. The alkaline phosphatase remaining associated with each individual well is then determined by conventional enzymatic methods. A MabSEC is selected which gives rise to the association of more alkaline phosphatase with the plate (and hence binding of MabProp-AP-Prop to the plate) in the presence of propranolol than in the absence of propranolol, and may, therefore, be used in the detection of propranolol.

EXAMPLE 5

Preparation and selection of a secondary monoclonal antibody for the assay of gentamicin.

The primary monoclonal antibody against gentamicin (MabGent) is obtained using as immunogen a gentamicin-bovine serum albumin conjugate made with 1-ethyl-3-(3-dimethylaminopropyl)carbodiimide (Sigma Chemical Company 1985 catalogue number E7750) in conventional manner. The MabGent is then conjugated to purified calf intestinal alkaline phosphatase. This is then used to raise secondary monoclonal antibodies and in the construction of an assay for gentamicin in an analogous manner to the previous example detailing the use of MabProp-AP in the assay of propranolol.

EXAMPLE 6

Preparation and selection of a secondary monoclonal antibody against a complex of propranolol and a primary monoclonal antibody against propranolol, said secondary monoclonal antibody not being an antibody against propranolol or the primary monoclonal antibody against propranolol.

Primary monoclonal antibody against propranolol (MabProp) is obtained by means of an immunogen consisting of a propranolol-bovine serum albumin conjugate madewith N-(4-bromobutyl)phthalimate (Sigma Chemical Co London catalogue number B 3502) by conventional means. Some of this antibody is conjugated to purified calf intestinal alkaline phosphatase. A 1 ml solution of 150 ug of MabProp in phosphate buffered saline at pH 7.4 is slowly mixed with constant gentle stirring with a 0.1 ml solution of 100 ug propranolol (prop). The mixture is left gently stirred at room temperature (23° C.) for 1 hour and then left at 4° C. for twelve hours, yielding MabProp-Prop complex. This is then used as immunogen in mice. The same hybridoma techniques as above are employed to give rise to cell lines producing monoclonal antibodies to the antibody-antigen complex (MabSEC). Culture fluids of these cell lines are then screened for their utility in the detection of propranolol in an analagous manner as the previous propranolol example.

EXAMPLE 7

Preparation and selection of a secondary monoclonal antibody against a complex of propranolol and a primary monoclonal antibody against propranolol, said secondary monoclonal antibody not being an antibody against propranolol or the primary monoclonal antibody against propranolol.

Primary monoclonal antibody against propranolol (MabProp) and secondary monoclonal antibodies against a complex of this with propranolol are obtained as in the previous example. The secondary antibodies are purified by conventional means and conjugated to purified calf intestinal alkaline phosphatase.

Microtitre plate are coated with the primary monoclonal antibody using the antibody coating method previously described. A range of propranolol standards from 0 to 100 ng/ml is made in 50 mM Tris buffer pH 7.4. 100 ul of each of these are placed in separate wells followed by 100 ul of a solution of conjugated secondary antibody. The mixtures are incubated at 37° C. for one hour and then shaken out. The wells are washed as previously described and the alkaline phosphatase remaining associated with each well determined. Secondary antibody alkaline phosphatase conjugates are thus identified which are of use in the detection of propranolol in being more retained in the wells in the presence of propranolol than in its absence.

EXAMPLE 8

Preparation of a monoclonal antibody against a complex of dihydrofolate reductase and methotrexate and an assay for methorexate based on that antibody.

Dihydrofolate reductase (DHFR) is obtained in a highly purified form by affinity chromatography with a methotrexate affinity column by conventional means. A complex is made of this and methotrexate is made by slowly mixing a solution of 150 ug of DHFR in 1 ml phosphate buffered saline with 50 ug methotrexate in the same volume and buffer. The mixture is then twice dialysed against 1 liter of phosphate buffered saline at 4° C. for four hours and then used as immunogen in mice to make monoclonal antibodies against the complex (MabSEC). The products are then screened for their usefulness in the detection of methotrexate as follows.

DHFR is bound to microtitre plates according to the method described in example 1 for antibody. Standard solutions of methotrexate in 50 mM Tris buffered saline pH 7.4 are made containing containing a range of methotrexate from 0 to 100 ng/ml. 100 ul of each of these are placed in duplicate wells on the coated plate followed by 100 ul of 50 mM Tris pH 7.4 containing 0.1% bovine serum albumin and 50 ng of MabSEC. The plate is incubated for one hour at 37° C. after which the solutions are shaken out and the wells washed four times with 50 mM Tris pH 7.4 continuing 0.02% Tween 20. 200 ul of a solution of anti-mouse IgG labelled with alkaline phosphatase (Sigma London catalogue number A 0532) at a 1:1000 dilution in 50 mM Tris pH 7.4 is then added and incubated at room temperature (23° C.) for a further hour. The solutions are shaken out and the plate washed as above a further four times and the alkaline phosphatase remaining associated with the wells determined. Those MabSEC antibodies which allow an assay for methotrexate to be carried out by virtue of causing more alkaline phsphatase to be associated with the wells in the presence of methotrexate than in its absence are thus identified.

EXAMPLE 9

Preparation and selection of a secondary monoclonal antibody for the determination of methotrexate.

This is carried out in an analogous manner to the previous example, however, instead of the labelled antibody being an anti-mouse IgG an alkaline phosphatase anti-mouse IgM is used (Sigma London catalogue number A 7784).

EXAMPLE 10

In an alternative form to example 4 the Fab fragment of the primary monoclonal antibody to propranol was formed and purified by conventional means and used throughout in place of the intact molecule.

I claim:

1. A secondary monoclonal antibody against a complex of a molecule of molecular weight less than 5000 and a binding protein against said molecule which secondary monoclonal antibody is not an antibody against molecule or against its binding protein.

2. A secondary monoclonal antibody according to claim 1 against a complex of a molecule of molecular weight less than 5000 and a monoclonal antibody against said molecule which secondary monoclonal antibody is not an antibody against said molecule or against its monoclonal antibody.

3. A secondary monoclonal antibody according to claim 2 wherein the molecule has a molecular weight less than 1200.

4. A secondary monoclonal antibody according to claim 2 wherein said molecule is a steroid.

5. A secondary monoclonal antibody according to claim 2 which has a signal generating label wherein the molecule of molecular weight less than 5000 has a molecular weight less than 1200.

6. A secondary antibody according to claim 5 wherein the molecule of molecular weight less than 5000 has a molecular weight less than 1200.

7. A secondary monoclonal antibody according to claim 5 wherein the signal generating label is a phosphatase.

8. A secondary antibody according to claim 1 wherein the molecule of molecular weight less than 5000 has a molecular weight less than 1200.

9. A secondary monoclonal antibody according to claim 2 wherein said molecule is a medicament.

10. A secondary antibody according to claim 9 wherein the molecule of molecular weight less than 5000 has a molecular weight less than 1200.

11. A secondary monoclonal antibody according to claim 2 wherein said molecule is progesterone.

12. A secondary monoclonal antibody according to claim 2 wherein said molecule is estrogen.

13. A secondary monoclonal antibody according to claim 2 wherein said molecule is hydrocortisone, testosterone, oestradiol, oestratriol or androstanediol.

14. A secondary monoclonal antibody according to claim 2 wherein said molecule is an aminoglycoside antibiotic.

15. A secondary monoclonal antibody according to claim 2 wherein said molecule is gentamycin.

16. A secondary monoclonal antibody according to claim 9 wherein said medicament is a cardioactive agent.

17. A secondary monoclonal antibody according to claim 2 wherein said molecule is digoxin.

18. A secondary monoclonal antibody according to claim 2 wherein said molecule is a drug of abuse.

19. A secondary monoclonal antibody according to claim 2 wherein the equilibrium constant between said antibody and said molecule or the monoclonal antibody thereto is less than $10^3$ liters per mole.

20. A secondary monoclonal antibody according to claim 2 wherein the equilibrium constant between said antibody and the complex of said molecule and its monoclonal antibody is at least $10^4$ liters per mole.

21. A secondary monoclonal antibody according to claim 2 wherein the ratio of equilibrium constant between the secondary monoclonal antibody and the complex and the secondary monoclonal antibody and either component of the complex is greater than 100:1.

22. A secondary monoclonal antibody according to claim 2 in the form of a freeze dried powder.

23. A secondary monoclonal antibody according to claim 2 which is a complete immunoglobulin.

24. A secondary monoclonal antibody according to claim 2 which is an antibody fragment.

25. A secondary monoclonal antibody according to claim 24 which is a Fab or $F(ab^1)_2$ fragment.

26. A secondary monoclonal antibody according to claim 1 which has a signal generating label.

27. A secondary monoclonal antibody according to claim 2 which has a signal generating label.

28. A secondary monoclonal antibody according to claim 27 wherein the signal generating label is an enzyme.

29. A secondary monoclonal antibody according to claim 28 wherein the enzyme is a phosphatase, peroxidase, galactosidase or dehydrogenase.

30. A secondary monoclonal antibody according to claim 28 wherein the enzyme is an alkaline phosphatase.

31. A secondary monoclonal antibody according to claim 27 wherein the signal generating label is a radiolabel.

32. A secondary monoclonal antibody according to claim 27 wherein the signal generating label is fluorescent.

33. A secondary monoclonal antibody according to claim 27 wherein the signal generating label is fluorescein.

34. A secondary monoclonal antibody according to claim 27 labeled with a chemiluminescent moiety.

35. A secondary monoclonal antibody according to claim 28 wherein the label is attached by means of a difunctional reagent.

36. A secondary monoclonal antibody according to claim 27 wherein the molecule is a steroid.

37. A secondary monoclonal antibody according to claim 27 wherein the molecule is a medicament.

38. A secondary monoclonal antibody according to claim 27 wherein the molecule is progesterone.

39. A secondary monoclonal antibody according to claim 27 wherein said molecule is an aminoglycoside antibiotic.

40. A secondary monoclonal antibody according to claim 27 wherein said molecule is digoxin.

41. A secondary monoclonal antibody according to claim 30 wherein said molecule is progesterone.

42. A diagnostic kit which contains a secondary monoclonal antibody according to claim 1 and said specific binding protein to the small molecule.

43. A secondary antibody according to claim 1 in the form of a freeze dried powder.

44. A method of determining a member of a pair consisting of a molecule of molecular weight less than 5000 or its binding protein which method comprises contacting a suspected source of a member of the pair with the other member of the pair to form a complex between the pair members and with a secondary monoclonal antibody to the complex of the pair which secondary monoclonal antibody is not an antibody against said molecule or against its binding protein and measuring the association between said complex and said secondary antibody.

45. A secondary antibody according to claim 44 wherein the molecule of molecular weight less than 5000 has a molecular weight less than 1200.

46. A method according to claim 44 of determining a molecule of molecular weight less than 5000 which comprises contacting a suspected source of said molecule with a primary monoclonal antibody to said molecule and with a secondary monoclonal antibody to the complex of said molecule and primary monoclonal antibody and measuring the association between said molecule and the primary and secondary monoclonal antibody, which secondary monoclonal antibody is not an antibody against the molecule or against its binding protein.

47. A method according to claim 46 wherein the secondary monoclonal antibody has a signal generating label.

48. A method of determining a molecule of molecular weight less than 5000 which comprises contacting a suspected source of said molecule with a monoclonal antibody therefore and with a secondary monoclonal antibody to a complex of said molecule and its monoclonal antibody which secondary monoclonal antibody is not an antibody against said molecule or its monoclonal antibody whereby the secondary monoclonal antibody, molecule and primary monoclonal antibody become associated, and measuring the association between said complex, and the secondary monoclonal antibody.

49. A method according to claim 48 wherein the secondary monoclonal antibody or primary monoclonal antibody has a signal generating label for measuring the association between said complex and the secondary monoclonal antibody.

50. A method according to claim 48 wherein the secondary monoclonal antibody has a signal generating label for measuring the association between said complex and said secondary monoclonal antibody.

51. A method according to claim 48 wherein the primary monoclonal antibody has a signal generating label for measuring the association between said complex and the said secondary monoclonal antibody.

52. A method according to claim 49 wherein the signal generating label is an alkaline phosphatase.

53. A method according to claim 49 wherein the signal generating label is an enzyme.

54. A method according to claim 49 wherein the signal generating label is fluorescent.

55. A method according to claim 49 wherein the signal generating label is chemiluminescent.

56. A method according to claim 53 wherein the signal generating label is an alkaline phosphatase.

57. A method according to claim 48 wherein the primary monoclonal antibody is bound to a surface, a liquid suspected source of said molecule is brought into contact with the surface and the secondary monoclonal antibody which has a signal generating label is also brought into contact with the surface, whereby said molecule and secondary monoclonal antibody become bound to the primary monoclonal antibody, the liquid is separated from the surface and the signal generating label is employed to measure the secondary monoclonal antibody.

58. A method according to claim 57 wherein the signal generating label is an enzyme.

59. A method according to claim 57 wherein the signal generating label is chemiluminescent.

60. A method according to claim 57 wherein the signal generating label is fluorescein.

61. A method according to claim 57 wherein the signal generating label is alkaline phosphatase.

62. A method according to claim 48 for determining a molecule of molecular weight less than 1200 which comprises binding a primary monoclonal antibody to said molecule to a surface, contacting the thus bound primary monoclonal antibody with a liquid suspected source of said molecule and with a secondary monoclonal antibody which has a signal generating label, incubating the system until said molecule and secondary monoclonal antibody become bound to the primary antibody and hence to the surface, separating the liquid from the surface and determining the secondary monoclonal antibody on the surface by employing the signal generating label.

63. A method according to claim 62 wherein the signal generating label is an enzyme.

64. A method according to claim 62 wherein the signal generating label is chemiluminescent.

65. A method according to claim 62 wherein the signal generating label is fluorescent.

66. A method according to claim 62 wherein the signal generating label is alkaline phosphatase.

67. A method according to claim 62 wherein said molecule is progesterone.

68. A method according to claim 66 wherein said molecule is progesterone.

69. A method, according to claim 48, for determining a molecule of molecular weight less than 1200, which comprises binding said secondary monoclonal antibody to a surface, contacting the thus bound secondary monoclonal antibody with a liquid suspected source of said molecule and with said primary monoclonal antibody, wherein said primary monoclonal antibody has a signal generating label, incubating the system until said molecule and primary monoclonal antibody become bound to said secondary monoclonal antibody and hence to said surface, separating the liquid from the surface and determining the primary monoclonal antibody on said surface by employing the signal generating label.

70. A method according to claim 69 wherein the signal generating label is an enzyme.

71. A method according to claim 69 wherein the signal generating label is alkaline phosphatase.

72. A method according to claim 69 wherein the signal generating label is chemiluminescent.

73. A method according to claim 69 wherein the signal generating label is fluorescent.

74. A method according to claim 69 wherein said molecule is progesterone.

75. A method according to claim 48 which is an elisa method.

76. A method according to claim 48 which is an agglutination method.

77. A method according to claim 48 carried out at 18°–25° C. in an aqueous solution at a pH of 5–9.

78. A method according to claim 48 wherein the molecule of molecular weight less than 5000 has a molecular weight less than 1200.

* * * * *